United States Patent
Chopin et al.

(10) Patent No.: US 6,740,312 B2
(45) Date of Patent: May 25, 2004

(54) TITANIUM DIOXIDE PARTICLES

(75) Inventors: Thierry Chopin, Saint-Leu-la-Foret (FR); Dominique Dupuis, Deuil-la-Barre (FR); Claudie Willemin, Paris (FR)

(73) Assignee: Rhodia Chimie, Courbevoie Cedex (FR)

( * ) Notice: Subject to any disclaimer, the term of this patent is extended or adjusted under 35 U.S.C. 154(b) by 0 days.

(21) Appl. No.: 10/172,499

(22) Filed: Jun. 17, 2002

(65) Prior Publication Data

US 2003/0082122 A1 May 1, 2003

Related U.S. Application Data

(63) Continuation of application No. 09/117,935, filed as application No. PCT/FR97/00266 on Feb. 12, 1997, now abandoned.

(30) Foreign Application Priority Data

Feb. 15, 1996 (FR) .............................. 96 01850

(51) Int. Cl.[7] .............................. A61K 7/42; A61K 9/15; A61K 9/16; C09C 1/36; C01G 23/047
(52) U.S. Cl. .................... 424/59; 106/436; 106/442; 423/610; 424/401; 424/489; 424/490; 502/350
(58) Field of Search ................ 424/401, 59, 489; 424/490; 423/610; 502/350; 106/436, 442

(56) References Cited

U.S. PATENT DOCUMENTS

| | | |
|---|---|---|
| 4,923,682 A | 5/1990 | Roberts et al. |
| 4,927,464 A | 5/1990 | Cowie |
| 5,100,858 A | 3/1992 | Chopin et al. |
| 5,149,519 A | 9/1992 | Chopin et al. |
| 5,188,831 A | 2/1993 | Nicoll et al. |
| 5,330,953 A | 7/1994 | Meina |
| 5,573,753 A | 11/1996 | Tapley |
| 5,616,532 A | 4/1997 | Heller et al. |
| 5,650,002 A | 7/1997 | Bolt |

FOREIGN PATENT DOCUMENTS

| | | |
|---|---|---|
| EP | 0 335 773 | 10/1989 |
| EP | 0 351 270 | 1/1990 |
| EP | 0 393 857 A | 10/1990 |
| EP | 0 401 045 | 12/1990 |
| EP | 0 748 624 | 12/1996 |

OTHER PUBLICATIONS

Database WPI, Week 8310, Derwent Publications Ltd., London, GB; AN 83–23326K, XP002017278 & JP 58 013 668 A (Horubein Kogyo), Jan. 26, 1983.

Database WPI, Week 8414, Derwent Publications Ltd., London, GB; AN 84–084520 XP002017279 & JP 59 033 364 A (Sanyo Shikiso), Feb. 23, 1984.

Database WPI, Week 9412, Derwent Publications Ltd., London, GB; AN 94–098009 XP002017280 & JP 06 049 388 A (Ishihara Sangyo Kaisha), Feb. 22, 1994.

Database WPI, Week 9403, Derwent Publications Ltd., London, GB; AN 94–022607 XP002033214 & JP 05 330 825 A (Ishihara Sangyo Kaisha), Dec. 14, 1993.

*Primary Examiner*—Thurman K. Page
*Assistant Examiner*—Marina Lamm
(74) *Attorney, Agent, or Firm*—Burns, Doane, Swecker & Mathis L.L.P.

(57) ABSTRACT

Anatase titanium dioxide particles with a size of at most 100 nm wherein the particles are at least partially covered with a layer of at least one metal oxide, hydroxide or hydroxide oxide and the particles exhibit a BET specific surface of at least 70 $m^2/g$ and a relative density of the order of 2.2. A process for preparing the anatase dioxide particles is also disclosed.

38 Claims, No Drawings

TITANIUM DIOXIDE PARTICLES

This application is a continuation of U.S. application Ser. No. 09/117,935, filed on Oct. 13, 1998, which was a national stage filing under 35 U.S.C. §371 of International Application No. PCT/FR97/00266 filed on Feb. 12, 1997, which International Application was not published by the International Bureau in English.

The present invention relates to novel anatase titanium dioxide particles exhibiting anti-UV properties which can be used in particular in cosmetic formulations.

It is known to use titanium dioxide as anti-UV agent in numerous applications, in particular in cosmetics, paint, plastics, and the like.

In these applications, the titanium dioxide is generally provided in the form of particles with a size of less than 100 nm as a dispersion in an aqueous or organic phase.

The problem resulting from the use of these dispersions of titanium dioxide particles arises from the fact that the latter are often unstable. To control their stability, it is known to add dispersing agents to them, generally organic polymers.

However, the addition of these dispersing agents is not a solution which is without its disadvantages. This is because, when the titanium dioxide dispersion is mixed with other products in order to prepare a cosmetic, paint or plastic formulation, this agent can exhibit behaviour incompatible with the application (stability, agglomeration, toxicity, and the like) or be incompatible with the other components of the formula.

In these applications, the need is thus felt to be able to have available dispersions of titanium dioxide particles which are stable without the addition of dispersing agent.

One aim of the present invention is thus to provide dispersions of titanium dioxide particles which are stable and which do not contain dispersing agent.

With this aim, the invention relates to anatase titanium dioxide particles with a size of at most 100 nm, the said particles being at least partially covered with a layer of at least one metal oxide, hydroxide or hydroxide oxide and exhibiting a BET specific surface of at least 70 m$^2$/g and a relative density of the order of 2.2.

With this aim, the invention also relates to the process for the preparation of these particles in which at least one metal oxide, hydroxide or hydroxide oxide is precipitated at the surface of anatase titanium dioxide particles with a size of at most 100 nm exhibiting a BET specific surface of at least 200 m$^2$/g and a relative density of the order of 2.5.

Finally, the invention also relates to the use of these particles as anti-UV agent in cosmetic, paint or varnish formulations and in plastics; and more particularly to an anti-UV cosmetic composition comprising particles according to the invention in an amount such that the content of titanium dioxide in the said composition is at least 1% and preferably at most 25% by weight.

The dispersions of particles according to the invention in addition exhibit the advantage of being stable over a wide pH range without addition of dispersing agent.

They can also exhibit high solids contents, while remaining stable and exhibiting a low viscosity, in particular of less than 1000 mPa·s.

Moreover, it is observed that these dispersions retain the same dispersion index even when they have been mixed with the components of a formulation, for example a cosmetic formulation.

Other characteristics, details and advantages of the invention will become more clearly apparent on reading the description and examples which will follow.

The invention first of all relates to anatase titanium dioxide particles with a size of at most 100 nm, the said particles being at least partially covered with a layer of at least one metal oxide, hydroxide or hydroxide oxide and exhibiting a BET specific surface of at least 70 m$^2$/g and a relative density of the order of 2.2.

The particles according to the invention are based on titanium dioxide with a largely anatase crystalline structure. "Largely" means that the level of anatase in the titanium dioxide particles of the coating is greater than 50% by mass. Preferably, the particles of the coating exhibit a level of anatase of greater than 80%. The degree of crystallization and the nature of the crystalline phase are measured by X-ray diffraction.

The mean diameter of these particles is at most 100 nm, preferably at least 25 nm, more preferably still between 50 and 70 nm. This diameter is measured by transmission electron microscopy (TEM).

The particles according to the invention exhibit a BET specific surface of at least 70 m$^2$/g, preferably of at least 100 m$^2$/g.

BET specific surface is understood to mean the specific surface determined by nitrogen adsorption in accordance with the ASTM standard D 3663-78 drawn up from the Brunauer-Emmett-Teller method described in the periodical "The Journal of the American Chemical Society", 60, 309 (1938). In order to measure the is specific surface of the particles according to the invention, when they are provided in the form of a dispersion, it is essential to follow the measuring protocol, which consists in removing the liquid phase from the dispersion and then in drying the particles under vacuum at a temperature of 150° C. for at least 4 hours.

The particles according to the invention also exhibit a relative density of the order of 2.2. "Of the order" is understood to mean that the relative density is 2.2+/−0.2. Such a relative density value is low with respect to the conventional relative density of anatase titanium dioxide, which is 3.8. This relative density is measured by picnometry.

The particles according to the invention are at least partially covered with an inorganic layer based on at least one metal oxide, hydroxide or hydroxide oxide. These metal oxides, hydroxides or hydroxide oxides can be chosen in particular from SiO$_2$, ZrO$_2$ or aluminium, zinc, titanium or tin oxides, hydroxides or hydroxide oxides, in the simple or mixed form. Mixed is understood to mean a metal compound based on at least two of the abovementioned elements (silicoaluminates, and the like).

In general, the ratio by weight of the metal oxide(s), hydroxide(s) or hydroxide oxide(s) to the titanium dioxide is at most 60% by weight. This ratio depends on the application for which the particles are intended. Preferably, when the particles are used in a cosmetic application, this ratio is at most 25%, more preferably still at most 20%.

This amount of metal oxide, hydroxide or hydroxide oxide is measured on the dispersed particles by X-ray fluorescence.

According to the preferred form of the invention, the particles are at least partially covered with a layer of silica and/or of an aluminium oxide, hydroxide or hydroxide oxide, in the simple or mixed form.

According to a preferred alternative form, the particles are covered with a layer of silica and of aluminium hydroxide or hydroxide oxide in contents by weight of 30% of SiO$_2$ and 15% of Al$_2$O$_3$ with respect to the titanium dioxide.

According to an even more preferred alternative form, the particles covered with a layer of silica and of aluminium hydroxide or hydroxide oxide in contents by weight of 15% of $SiO_2$ and 5% of $Al_2O_3$ with respect to the titanium dioxide are particularly advantageous.

According to the preferred form of the invention, the particles are provided in the form of a dispersion.

This dispersion generally exhibits a conductivity of at most 3 msiemens.

This dispersion can exhibit a proportion of suspended solid (solids content) of between 10 and 60% by weight, preferably of at least 35%, more preferably still of at least 40%.

The dispersions of particles according to the invention exhibiting a solids content of at least 35% have the advantage of being only very slightly viscous; thus, their viscosity is generally at most 1000 mPa·s.

This dispersion generally exhibits a dispersion index of the particles in the liquid phase of at most 0.5.

The dispersion index is determined by the formula:

$$I = \frac{\varnothing_{84} - \varnothing_{16}}{2\varnothing_{50}}$$

in which:

$\varnothing_{84}$ is the diameter of the particles for which 84% of the particles have a diameter of less than $\varnothing_{84}$, $\varnothing_{16}$ is the diameter of the particles for which 16% of the particles have a diameter of less than $\varnothing_{16}$, $\varnothing_{50}$ is the mean diameter of the particles.

The diameters of use in the determination of the dispersion index are measured by centrifugal sedimentation of the particles of the dispersion, monitored by X-rays, using a Brookhaven type XDC device.

Such an index reflects the good dispersibility of the particles. In the case of aqueous dispersions, this index is obtained over a wide pH range which can vary from 5.5 to 10. The dispersions are stable and they retain this index value over time, despite the absence of dispersing agent.

The particles according to the invention can also be agglomerated and be provided in the form of a powder. The size of the agglomerates can be between 1 and 40 μm, measured by TEM.

Following an organic treatment, this powder can exhibit good redispersibility in water or in organic medium. This organic treatment can be carried out, for example, by atomization in the presence of a fatty acid, such as stearic acid, or of a metal salt of a fatty acid or alternatively by grafting a trialkoxysilane, and the like.

The invention also relates to the process for the preparation of these particles, which consists in precipitating at least one metal oxide, hydroxide or hydroxide oxide at the surface of anatase titanium dioxide particles with a size of at most 120 nm exhibiting a BET specific surface of at least 200 $m^2/g$ and a relative density of the order of 2.5.

This precipitation can be carried out by:

introducing, into a dispersion of particles of titanium dioxide exhibiting the characteristics defined hereinabove, precursors of the metal oxides, hydroxides or hydroxide oxides, generally in the form of aqueous salt solutions, then, modifying the pH in order to obtain the precipitation of these oxides, hydroxides or hydroxide oxides on the titanium dioxide particles.

This precipitation is generally carried out at a temperature of at least 50° C.

In the case of the precipitation of silica and of an aluminium hydroxide or hydroxide oxide, the precipitation can be carried out at acidic or basic pH. The pH is controlled by the addition of an acid, such as sulphuric acid, or by the simultaneous and/or alternating introduction of an alkaline compound of silicon and of an acidic compound of aluminium. In this case, the pH is preferably between 8 and 10.

The silica can be precipitated from a silicon salt, such as an alkaline silicate.

The aluminium hydroxide or hydroxide oxide can be precipitated from an aluminium salt, such as aluminium sulphate, sodium aluminate, basic aluminium chloride or aluminium diacetate hydroxide.

It is possible, after the precipitation, to recover and wash the particles obtained following the treatment, before redispersing them. This stage can be carried out by centrifuging and washing or, preferably, by washing by ultrafiltration. The pH of the aqueous wash liquor is advantageously of the order of 5.5. The particles are then redispersed in another liquid medium, so as to obtain a dispersion of titanium dioxide particles. This liquid medium can be acidic or basic; it is preferably a basic solution exhibiting a pH of the order of 8–9.

To obtain a powder of particles according to the invention, the dispersion resulting from the process is dried, generally at a temperature of less than 110° C.

The starting anatase titanium dioxide particles must exhibit a size of at most 100 nm, a BET specific surface of at least 200 $m^2/g$ and a relative density of the order of 2.5.

The starting particles are based on titanium dioxide with a mainly anatase crystalline structure, as defined above.

The mean diameter of these particles is at most 100 nm, preferably at least 25 nm, more preferably still between 50 and 70 nm. This diameter is measured by transmission electron microscopy (TEM).

The starting particles exhibit a BET specific surface of at least 200 $m^2/g$, preferably of at least 250 $m^2/g$.

This BET specific surface is measured in the same way as defined above.

The starting particles also exhibit a relative density of the order of 2.5. "Of the order" is understood to mean that the relative density is 2.5+/−0.2. This relative density is given by the following formula:

$$\text{relative density} = \frac{1}{(1/\rho) + Vi}$$

in which:

ρ is the relative density of the anatase, i.e. 3.8,

Vi is the volume contributed by the intraparticle pores; it is measured by the BJH method. Volume measured by the BJH method is understood to mean the volume measured from the Barrett-Joyner-Helenda method described in the article in the work Techniques de l'Ingénieur [Techniques of the Engineer] and entitled "Texture des solides poreux ou divisés" [Texture of porous or divided solids], p.3645-1 to 3645-13.

In order to measure the volume contributed by the intraparticle pores of the particles according to the invention, when they are provided in the form of a dispersion, it is essential to follow the measuring protocol which consists in removing the liquid phase from the dispersion and then in drying the particles under vacuum at a temperature of 150° C. for at least 4 hours.

Such particles can be obtained by hydrolysis of at least one titanium compound A in the presence of at least one compound B chosen from:

(i) the acids which exhibit:

either a carboxyl group and at least two hydroxyl and/or amine groups, or at least two carboxyl groups and at least one hydroxyl and/or amine group, (ii) the organic phosphoric acids of following formulae:

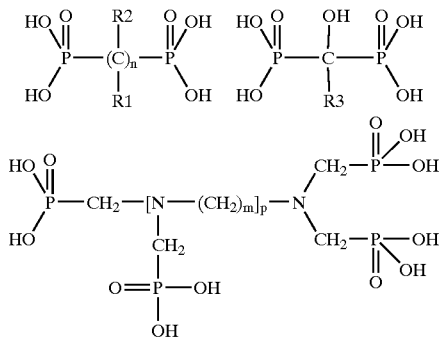

in which n and m are integers of between 1 and 6 and p is an integer of between 0 and 5, R1, R2 and R3, which are identical or different, representing a hydroxyl, amino, aralkyl, aryl or alkyl group or hydrogen, (iii) the compounds capable of releasing sulphate ions in acidic medium, (iv) the salts of the acids described above, and in the presence of anatase titanium dioxide seeds exhibiting a size of at most 8 nm and in a titanium, expressed as $TiO_2$, present in the seeds/titanium present before introduction of the seeds in the hydrolysis medium, expressed as $TiO_2$, ratio by weight of between 0.0% and 3%.

The starting solution, intended to be hydrolysed, is preferably completely aqueous; it is optionally possible to add another solvent, for example an alcohol, provided that the titanium compound A and the compound B used are then substantially soluble in this mixture.

As regards the titanium compound A, use is generally made of a compound chosen from titanium halides, oxyhalides or alkoxides, sulphates and more particularly synthetic sulphates.

Synthetic sulphates are understood to mean titanyl sulphate solutions prepared by ion exchange from very pure titanium chloride solutions or by reaction of sulphuric acid with a titanium alkoxide.

The preparation is preferably carried out with titanium compounds of the titanium halide or oxyhalide type. The titanium halides or oxyhalides which are more particularly used in the present invention are titanium fluorides, chlorides, bromides and iodides (respectively oxyfluorides, oxychlorides, oxybromides and oxyiodides).

According to a particularly preferred form, the titanium compound is titanium oxychloride $TiOCl_2$.

The amount of titanium compound A present in the solution to be hydrolysed is not critical.

The initial solution additionally contains at least one compound B as defined above. Mention may be made, as non-limiting examples of compounds B coming within the scope-of the present invention, of in particular:

hydroxypolycarboxylic acids and more particularly hydroxydi- or hydroxytricarboxylic acids, such as citric acid, maleic acid and tartaric acid, (polyhydroxy)monocarboxylic acids, such as, for example, glucoheptonic acid and gluconic acid, poly(hydroxycarboxylic) acids, such as, for example, tartaric acid, dicarboxylic monoacids and their corresponding amides, such as, for example, aspartic acid, asparagine and glutamic acid, hydroxylated or non-hydroxylated monocarboxylic amino acids, such as, for example, lysine, serine and threonine, aminotri(methylenephosphonate), ethylenediaminotetra (methylenephosphonate), triethylenetetraaminohexa (methylenephosphonate), tetraethylenepentaaminohepta(methylenephosphonate) or pentaethylenehexaaminoocta (methylenephosphonate), methylenediphosphonate, 1,1'-ethylenediphosphonate, 1,2-ethylenediphosphonate, 1,1'-propylenediphosphonate, 1,3-propylenediphosphonate, 1,6-hexamethylenediphosphonate, 2,4-dihydroxypentamethylene-2,4-diphosphonate, 2,5-dihydroxyhexamethylene-2,5-diphosphonate, 2,3-dihydroxybutylene-2,3-diphosphonate, 1-hydroxybenzyl-1,1'-diphosphonate, 1-aminoethylene-1,1'-diphosphonate, hydroxymethylenediphosphonate, 1-hydroxyethylene-1,1'-diphosphonate, 1-hydroxypropylene-1,1'-diphosphonate, 1-hydroxybutylene-1,1'-diphosphonate or 1-hydroxyhexamethylene-1,1'-diphosphonate.

As already indicated, it is also possible to use, as compound B, all the salts of the abovementioned acids. In particular, these salts are either alkali metal salts, more particularly sodium salts, or ammonium salts.

These compounds can also be chosen from sulphuric acid and ammonium or potassium sulphates, and the like.

The compounds B as defined above are preferably hydrocarbon-comprising compounds of aliphatic type. In this case, the length of the main hydrocarbon-comprising chain preferably does not exceed 15 carbon atoms and more preferably 10 carbon atoms. The preferred compound B is citric acid.

The amount of compound B is not critical. The molar concentration of the compound B with respect to that of the titanium compound A is generally between 0.2 and 10% and preferably between 1 and 5%.

Finally, the starting solution comprises titanium dioxide seeds used in a specific way.

Thus, the titanium dioxide seeds used in the present invention must first of all exhibit a size of less than 8 nm, measured by X-ray diffraction. Use is preferably made of titanium dioxide seeds exhibiting a size of between 3 and 5 nm.

Subsequently, the ratio by weight of the titanium dioxide present in the seeds to the titanium present in the hydrolysis medium before introduction of the seeds, that is to say contributed by the titanium compound A, and expressed as $TiO_2$ is between 0.01 and 3%. This ratio can preferably be between 0.05 and 1.5%. The bringing together of these two conditions with respect to the seeds (size and ratio by weight), in combination with the process as described above, makes it possible to precisely control the final size of the titanium dioxide particles, a level of seeds being associated with a particle size. It is thus possible to obtain particles for which the size varies between 25 and 100 nm.

Use is made of titanium dioxide seeds in the anatase form, so as to induce precipitation of the titanium dioxide in the anatase form. Generally, due to their small size, these seeds instead exist in the form of poorly crystallized anatase. The seeds are generally provided in the form of an aqueous suspension composed of titanium dioxide. They can generally be obtained in a known way by a process of neutralization of a titanium salt by a base.

The following stage consists in hydrolysing this starting solution by any means known to a person skilled in the art and generally by heating. In the latter case, the hydrolysis can preferably be carried out at a temperature greater than or equal to 70° C. It is also possible to operate, firstly, at a temperature below the boiling temperature of the medium and, then, to maintain the hydrolysis medium level at the boiling temperature.

Once hydrolysis has been carried out, the titanium dioxide particles obtained are recovered by separation of the precipitated solid from the mother liquors before being redispersed in a liquid medium so as to obtain a titanium dioxide dispersion. This liquid medium can be acidic or basic. It is preferably a basic solution, for example an aqueous sodium hydroxide solution. It is from this dispersion that the stage of precipitation of the metal oxides, hydroxides or hydroxide oxides will be carried out.

According to a specific alternative form, after the recovery of the particles obtained following the hydrolysis and before they are redispersed, the particles are neutralized and subjected to at least one washing operation. The particles can be recovered, for example by centrifuging the solution resulting from the hydrolysis; they are subsequently neutralized with a base, for example a sodium hydroxide or aqueous ammonia solution, they are then washed by redispersing them in an aqueous solution, and finally the particles are separated from the aqueous washing phase. After optionally one or more other washing operations of the same type, the particles are redispersed in an acidic or basic solution.

These particles generally exhibit a high degree of purity, compatible with an application in cosmetics.

Finally, the invention relates to the use of the particles described above as anti-UV agent. They can be used in particular as anti-UV agent in cosmetic, varnish or paint formulations and in plastics.

Introduced into cosmetic formulations, these titanium dioxide dispersions or powders make it possible to obtain an SPF (Sun Protection Factor) number of at least 20.

Moreover, the formulations obtained are photostable, that is to say that they do not exhibit blueing after exposure to UV according to the test defined in the examples.

They are particularly stable on storage and it may be observed that the titanium dioxide particles retain their dispersion index in the formulation.

The invention relates to anti-UV cosmetic compositions comprising particles as described above in an amount such that the titanium dioxide content in the said compositions is at least 1%, preferably at most 25%, by weight and more preferably still between 2 and 10% by weight.

It is possible to introduce into the cosmetic compositions particles exhibiting different particle sizes.

The compositions forming the subject-matter of the invention can be formulated as a large number of types of products, such as anti-sun products of gel, lotion, oil or cream type and more generally make-up products, self-tanning agents, care products, hairs, total blocks for the lips and many other compositions of the same type.

The term cosmetic composition or formulation is understood to mean all cosmetic products or preparations, such as those described in Appendix I ("Illustrative list by category of cosmetic products") of European Directive No. 76/768/EEC of Jul. 27, 1976, known as the cosmetic directive.

The cosmetic compositions forming the subject-matter of the invention can involve a vehicle, or a mixture of several vehicles, which act as diluent, dispersant or support for the other constituents of the composition and make possible their distribution when the composition is spread over the skin or hair.

The vehicles other than water can be liquid or solid emollients, solvents, humectants, thickeners or powders. The following types of vehicles can be used, for example, alone or as a mixture:

emollients, such as stearyl alcohol, glyceryl monoricinoleate, oleyl alcohol, cetyl alcohol, isopropyl isostearate, stearic acid, isobutyl palmitate, isocetyl stearate, isopropyl laurate, hexyl laurate, decyl oleate, octadecan-2-ol, isocetyl alcohol, eicosanyl alcohol, behenyl alcohol, cetyl palmitate, silicone oils, such as dimethylpolysiloxane, di-n-butyl sebacate, isopropyl myristate, isopropyl palmitate, isopropyl stearate, butyl stearate, polyethylene glycol, lanolin, cacao butter, cottonseed oil, olive oil, palm oil, rapeseed oil, soybean oil, sunflower oil, avocado oil, almond oil, sesame oil, coconut oil, groundnut oil, castor oil, mineral oil, butyl myristate, isostearic acid, palmitic acid, isopropyl linoleate, lauryl lactate, decyl oleate or myristyl myristate;

propellants, such as: propane, butane, isobutane, dimethyl ether, carbon dioxide or nitrogen dioxide;

solvents, such as: ethanol, methylene chloride, isopropanol, acetone, ethylene glycol monoethyl ether, diethylene glycol monobutyl ether, diethylene glycol monoethyl ether, dimethyl sulphoxide, dimethylformamide or tetrahydrofuran;

powders, such as chalk, talc, kaolin, starch, gums, colloidal silica, poly(sodium acrylate), tetraalkyl- and/or trialkylarylammonium smectites, chemically modified magnesium aluminosilicate, organically modified montmorillonite, hydrated aluminium silicate, pyrogenic silica, polycarboxyvinyl, sodium carboxymethylcellulose or ethylene glycol monostearate.

The compositions according to the invention generally comprise from 10 to 99% by weight of at least one vehicle as described above.

The compositions according to the invention are preferably provided in the form of emulsions, in which an oily component is present with an emulsifier, so as to form an oil-in-water or water-in-oil emulsion, depending on the value of the hydrophile/lipophile balance (HLB).

Thus, the compositions according to the invention can comprise one or more oily components or components having the properties of an oil.

It can relate to vegetable or mineral oils, such as those provided in the above list of emollients. It is also possible to use volatile or non-volatile silicone oils, such as polydimethylsiloxanes.

These oily components can represent up to 90%, preferably from 10 to 80%, of the volume of the composition.

The compositions according to the invention can also comprise one or more emulsifiers. Depending on the nature of these emulsifiers, the compositions will be provided in the form of an oil-in-water or water-in-oil emulsion.

For the preparation of an emulsion of water-in-oil type, the emulsifier or emulsifiers chosen must exhibit a mean HLB of between 1 and 6. For the preparation of an emulsion of oil-in-water type, the emulsifier or emulsifiers chosen must exhibit a mean HLB greater than 6. The amount of these emulsifiers in the compositions according to the invention can vary between 1 and 50% by weight, preferably between 2 and 20%.

These cosmetic compositions can also comprise surface-active agents which serve to disperse, emulsify, dissolve or stabilize various compounds used for their emollient or humectant properties. These surface-active agents are used in these compositions at concentrations varying from 0.05 to 50% by weight of the preparation. Anionic, non-ionic, cationic, zwitterionic or amphoteric surfactants or mixtures of these surfactants are thus found, such as:

anionic surfactants:

alkyl ester sulphonates of formula R—CH(SO$_3$M)—COOR', where R represents a $C_8$–$C_{20}$, preferably $C_{10}$–$C_{16}$, alkyl radical, R' a $C_1$–$C_6$, preferably $C_1$–$C_3$, alkyl radical and M an alkali metal cation (sodium, potassium or lithium), substituted or unsubstituted ammonium -(methyl-, dimethyl-, trimethyl- or tetramethylammonium, dimethylpiperidinium, and the like) or derivative of an alkanolamine (monoethanolamine, diethanolamine, triethanolamine and the like). Mention may very particularly be made of methyl ester sulphonates in which the R radical is $C_{14}$–$C_{16}$;

alkyl sulphates of formula ROSO$_3$M, where R represents a $C_{10}$–$C_{24}$, preferably $C_{12}$–$C_{20}$ and very particularly $C_{12}$–$C_{18}$ alkyl or hydroxyalkyl radical, M representing a hydrogen atom or a cation with the same definition as above, and their oxyethylenated (EO) and/or oxypropylenated (PO) derivatives exhibiting, on average, from 0.5 to 6, preferably from 0.5 to 3, EO and/or PO units;

alkylamide sulphates of formula RCONHR'OSO$_3$M, where R represents a $C_2$–$C_{22}$, preferably $C_6$–$C_{20}$, alkyl radical and R' a $C_2$–$C_3$ alkyl radical, M representing a hydrogen atom or a cation with the same definition as above, and their oxyethylenated (EO) and/or oxypropylenated (PO) derivatives exhibiting, on average, from 0.5 to 60 EO and/or PO units;

salts of saturated or unsaturated $C_8$–$C_{24}$, preferably $C_{14}$–$C_{20}$, fatty acids, $C_9$–$C_{20}$ alkylbenzenesulphonates, primary or secondary $C_8$–$C_{22}$ alkyl sulphonates, alkyl glycerol sulphonates, the sulphonated polycarboxylic acids described in GB-A-1,082,179, paraffin sulphonates, N-acyl-N-alkyltaurates, alkyl phosphates, alkyl isethionates, alkyl succinamates, alkyl sulphosuccinates, monoesters or diesters of sulphosuccinates, N-acylsarcosinates, sulphates of alkyl glycosides or polyethoxycarboxylates, the cation being an alkali metal (sodium, potassium or lithium), a substituted or unsubstituted ammonium residue (methyl-, dimethyl-, trimethyl- or tetramethylammonium, dimethylpiperidinium, and the like) or derivative of an alkanolamine (monoethanolamine, diethanolamine, triethanolamine, and the like);

non-ionic surface-active agents:

polyoxyalkylenated (polyoxyethylenated, polyoxypropylenated or polyoxybutylenated) alkylphenols, the alkyl substituent of which is $C_6$–$C_{12}$, containing from 5 to 25 oxyalkylene units; mention may be made, by way of example, of Triton X-45, Triton X-114, Triton X-100 or Triton X-102 sold by Rohm & Haas Cy.;

glucosamides or glucamides;

glycerolamides derived from N-alkylamines (U.S. Pat. No. 5,223,179 and FR-A-1,585,966);

polyoxyalkylenated $C_8$–$C_{22}$ aliphatic alcohols containing from 1 to 25 oxyalkylene (oxyethylene or oxypropylene) units; mention may be made, by way of example, of Tergitol 15-S-9 or Tergitol 24-L-6 NMW, sold by Union Carbide Corp., Neodol 45-9, Neodol 23-65, Neodol 45-7 or Neodol 45-4, sold by Shell Chemical Cy., or Kyro EOB, sold by The Procter & Gamble Cy.;

the products resulting from the condensation of ethylene oxide with a hydrophobic compound resulting from the condensation of propylene oxide with propylene glycol, such as the Pluronic sold by BASF;

amine oxides, such as ($C_{10}$–$C_{18}$ alkyl)-dimethylamine oxides or ($C_8$–$C_{22}$ alkoxy)-ethyldihydroxyethylamine oxides;

the alkyl polyglycosides described in U.S. Pat. No. 4,565,647 and their polyoxyalkylenated derivatives;

amides of $C_8$–$C_{20}$ fatty acids;

ethoxylated fatty acids;

ethoxylated amides, amines or amidoamines;

amphoteric and zwitterionic surface-active agents:

alkyltrimethylsulphobetaines, condensation products of fatty acids and of protein hydrolysates, alkyl amphopropionates or -dipropionates, alkyl sultaines, or amphoteric derivatives of alkylpolyamines, such as Amphionic XL®, sold by Rhône-Poulenc, or Ampholac 7T/X® and Ampholac 7C/X®, sold by Berol Nobel, are used to decrease the irritation caused by other surface-active agents, mainly anionic surface-active agents.

Use may also be made of an emulsifier chosen from those on the following list:

| Chemical name of the emulsifier | Trade name | HLB |
| --- | --- | --- |
| Sorbitan trioleate | Arlacel 85 | 1.8 |
| Sorbitan tristearate | Span 65 | 2.1 |
| Glycerol monooleate | Aldo MD | 2.7 |
| Glycerol monostearate | Atmul 84S | 2.8 |
| Glycerol monolaurate | Aldo MC | 3.3 |
| Sorbitan sesquioleate | Arlacel 83 | 3.7 |
| Sorbitan monooleate | Arlacel 80 | 4.3 |
| Sorbitan monostearate | Arlacel 60 | 4.7 |
| Polyoxyethylene stearyl ether | Brij 72 | 4.9 |
| Polyoxyethylene sorbitol derivative of beeswax | G-1702 | 5 |
| Polyglyceryl-3 diisostearate | Plurol Diisostearic | 6 |
| PEG 200 dilaurate | Emerest 2622 | 6.3 |
| Sorbitan monopalmitate | Arlacel 40 | 6.7 |
| PEG 200 monostearate | Tegester PEG 200 MS | 8.5 |
| Sorbitan monolaurate | Arlacel 200 | 8.6 |
| PEG 400 dioleate | Tegester PEG 400-DO | 8.8 |
| Polyoxyethylene (5) monostearate | Ethofat 60-16 | 9.0 |
| Polyoxyethylene (4) sorbitan monostearate | Tween 61 | 9.6 |
| Polyoxyethylene (4) lauryl ether | Brij 30 | 9.7 |
| Polyoxyethylene (5) sorbitan monooleate | Tween 81 | 10.0 |
| PEG 300 monooleate | Neutronyx 834 | 10.4 |
| Polyoxyethylene (20) sorbitan tristearate | Tween 65 | 10.5 |
| Polyoxyethylene (20) sorbitan trioleate | Tween 85 | 11.0 |
| Polyoxyethylene monostearate | Myrj 45 | 11.1 |
| PEG 400 monooleate | Emerest 2646 | 11.7 |
| PEG 400 monostearate | Tegester PEG 400 | 11.9 |
| Polyoxyethylene (10) monooleate | Ethofat 0/20 | 12.2 |
| Polyoxyethylene (10) stearyl ether | Brij 76 | 12.4 |
| Polyoxyethylene (10) cetyl ether | Brij 56 | 12.9 |

-continued

| Chemical name of the emulsifier | Trade name | HLB |
|---|---|---|
| Polyoxyethylene (4) sorbitan monolaurate | Tween 21 | 13.3 |
| PEG 600 monooleate | Emerest 2660 | 13.7 |
| PEG 1000 dilaurate | Kessco | 13.9 |
| Polyoxyethylene sorbitol derivative of lanolin | G-1441 | 14.0 |
| Polyoxyethylene (12) lauryl ether | Ethosperse LA-12 | 14.4 |
| PEG 1500 dioleate | Pegosperse 1500 | 14.6 |
| Polyoxyethylene (14) laurate | Arosurf HFL-714 | 14.8 |
| Polyoxyethylene (20) sorbitan monostearate | Tween | 14.9 |
| Polyoxyethylene (20) sorbitan monooleate | Tween 80 | 15.0 |
| Polyoxyethylene (20) stearyl ether | Brij 78 | 15.3 |
| Polyoxyethylene (20) sorbitan monopalmitate | Tween 40 | 15.6 |
| Polyoxyethylene (20) cetyl ether | Brij 58 | 15.7 |
| Polyoxyethylene (25) oxypropylene | Monostearate G-2162 | 16.0 |
| Polyoxyethylene (20) sorbitol monolaurate | Tween 20 | 16.7 |
| Polyoxyethylene (23) lauryl ether | Brij 35 | 16.9 |
| Polyoxyethylene (50) monostearate | Myrj 53 | 17.9 |
| PEG 4000 monostearate | Pegosperse 4000 MS | 18.7 |

The compositions according to the invention can comprise water in a content which can range up to 80% by volume, preferably between 5 and 80%.

The compositions according to the invention can additionally comprise a high molecular weight silicone surface-active agent which can be an emulsifier used instead of those mentioned hereinabove.

This agent can be a high molecular weight dimethylpolysiloxane with polyoxyethylene and/or polyoxypropylene chains having a molecular weight of between 10,000 and 50,000 and with the structure:

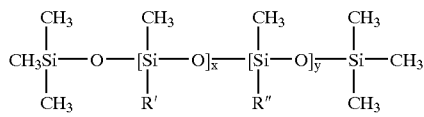

in which:
the R' and R" groups are chosen from H, $C_1$–$C_{18}$ alkyl and $[CH_2CH_2O]_a[CH_2CH(CH_3)O]_bH$; one of the R' and R" groups can be lauryl, the other having a molecular weight of between 1000 and 5000,
a is between 9 and 115, preferably between 10 and 114,
b is between 0 and 50, preferably between 0 and 49,
x is between 133 and 673, preferably between 388 and 402,
y is between 25 and 0.25, preferably between 15 and 0.75.

The dimethylpolysiloxane can be used in the form of a dispersion in a volatile siloxane, this dispersion comprising from 1 to 20% by volume of dimethylpolysiloxane.

The dimethylpolysiloxanes can be chosen from cyclomethicone and dimethicone copolyols, such as DC 3225C from Dow Corning, or lauryl methicone copolyol, such as DC Q2-5200 from Dow Corning.

It can also relate to Mirasil DMCO from Rhône-Poulenc or the cetyl dimethicone copolyol Abil AM90 from Th. Goldschmidt AG.

The composition according to the invention can comprise up to 25% by weight of such a surface-active agent.

The compositions according to the invention can also comprise an organic sunscreen, such as, for example:

| CTFA Name | Trade name | Sold by |
|---|---|---|
| 3-Benzophenone | Uvinul M-40 | BASF |
| 4-Benzophenone | Uvinul MS-40 | BASF |
| 8-Benzophenone | Spectra-Sorb UV-24 | American Cyanamid |
| Glyceryl PABA | Nipa GMPA | Nipa Labs |
| Octocrylene | Uvinul N-539 SG | BASF |
| Octyl dimethyl PABA | Escalol 507 | ISP |
| Octyl methoxycinnamate | Parsol MCX | Givaudan/Roux |
| Octyl salicylate | Uvinul O-18 | BASF |
| PABA | No. 102 | Merck |
| 2-Phenylbenz-imidazole-5-sulphonic acid | Eusolex 232 | Merck |
| 3-(4-Methylbenz-ylidene)camphor | Eusolex 6300 | EM Ind. |
| 4-Isopropyldi-benzoylmethane | Eusolex 8020 | EM Ind. |
| Butylmethoxydi-benzoylmethane | Parsol 1789 | Givaudan/Roux |
| Etocrylene | Uvinul N-35 | BASF |

It is also possible to use, as sunscreen, any compound authorized in European Directive No. 76/768/EEC and its appendices.

The composition according to the invention can also comprise inorganic sunscreens, such as: zinc oxide in the form of particles with a mean size of between 1 and 300 nm, iron oxide in the form of particles with a mean size of between 1 and 300 nm and silica in the form of particles with a mean size of between 1 and 100 nm.

The compositions can also comprise additives, such as:
preservatives, for example para-hydroxybenzoate esters;
antioxidants, such as butylhydroxytoluene;
humectants, such as glycerol, sorbitol, dibutyl phthalate, gelatin or PEGs, for example PEGs 200–600;
buffer solutions, such as mixtures of lactic acid and of sodium hydroxide or of triethanolamine;
waxes, such as beeswax or paraffin wax;
plant extracts;
preservatives, such as the methyl, ethyl, propyl and butyl esters of p-hydroxybenzoic acid, sodium benzoate, Germaben (trade name) or any chemical agent which prevents bacterial proliferation or moulds and which is conventionally used in cosmetic compositions, are generally introduced into these compositions at a level of 0.01 to 3% by weight. The amount of these products is generally adjusted in order to prevent any proliferation of bacteria, moulds or yeasts in the cosmetic compositions. As an alternative to these chemical agents, it is sometimes possible to use agents which modify the activity of the water and which greatly increase the osmotic pressure, such as carbohydrates or salts;
. . .

The cosmetic compositions forming the subject-matter of the invention can also comprise fixative resins. These fixative resins are generally present at concentrations of between 0.01 and 10%, preferably between 0.5 and 5%. The constituent fixative resins of the cosmetic compositions forming the subject-matter of the invention are preferably chosen from the following resins: acrylate/acrylamide copolymer, poly(vinyl methyl ether)/maleic anhydride copolymer, vinyl acetate/crotonic acid copolymer, octylacrylamide/acrylate/butylaminoethyl methacrylate copolymer, polyvinylpyrrolidone (PVP), copolymers of polyvinylpyrrolidone and of methyl methacrylate, copolymer of polyvinylpyrrolidone and of vinyl acetate (VA), poly(vinyl alcohol), copolymer of poly(vinyl alcohol) and of crotonic acid, copolymer of poly(vinyl alcohol) and of maleic anhydride, hydroxypropyl cellulose, hydroxypropyl guar, sodium polystyrenesulphonate, polyvinylpyrrolidone/ethyl methacrylate/methacrylic acid terpolymer, monomethyl ether of poly(methyl vinyl ether—maleic acid), poly (ethylene glycol terephthalate)/poly(ethylene glycol) copolymers, poly(ethylene glycol terephthalate)/poly (ethylene glycol)/poly(sodium sulphoisophthalate) copolymers, and their mixtures. The fixative resins can also comprise grafted functionalized polyorganosiloxane units, as described in Patent WO 95/06079.

The fixative resins will preferably be of the following type: polyvinylpyrrolidone (PVP), copolymers of polyvinylpyrrolidone and of methyl methacrylate, copolymer of polyvinylpyrrolidone and of vinyl acetate (VA), poly (ethylene glycol terephthalate)/poly(ethylene glycol) copolymers, poly(ethylene glycol terephthalate)/poly (ethylene glycol)/poly(sodium sulphoisophthalate) copolymers, and their mixtures.

These fixative resins are preferably dispersed or dissolved in the chosen vehicle.

The cosmetic compositions forming the subject-matter of the invention can also comprise polymeric derivatives exercising a protective function.

These polymeric derivatives can be present in amounts of the order of 0.01 to 10%, preferably approximately 0.1 to 5% and very particularly of the order of 0.2 to 3% by weight, agents such as cellulose derivatives, such as cellulose hydroxyethers, methylcellulose, ethylcellulose, hydroxypropyl methylcellulose or hydroxybutyl methylcellulose poly(vinyl ester)s grafted onto polyalkylene backbones, such as poly(vinyl acetate)s grafted onto polyoxyethylene backbones (EP-A-219,048)

poly(vinyl alcohol)s polyester copolymers based on ethylene terephthalate and/or propylene terephthalate and polyoxyethylene terephthalate units, with an ethylene terephthalate and/or propylene terephthalate (number of units)/polyoxyethylene terephthalate (number of units) molar ratio of the order of 1/10 to 10/1, preferably of the order of 1/1 to 9/1, the polyoxyethylene terephthalates exhibiting polyoxyethylene units having a molecular weight of the order of 300 to 5000, preferably of the order of 600 to 5000 (U.S. Pat. Nos. 3,959,230, 3,893,929, 4,116,896, 4,702,857 and 4,770,666);

sulphonated polyester oligomers obtained by sulphonation of an oligomer derived from ethoxylated allyl alcohol, dimethyl terephthalate and 1,2-propylenediol exhibiting from 1 to 4 sulpho groups (U.S. Pat. No. 4,968,451)

polyester copolymers based on propylene terephthalate and polyoxyethylene terephthalate units and terminated by ethyl or methyl units (U.S. Pat. No. 4,711,730) or polyester oligomers terminated by alkyl polyethoxy groups (U.S. Pat. No. 4,702,857) or anionic sulphopolyethoxy (U.S. Pat. No. 4,721,580) or anionic sulphoaroyl (U.S. Pat. No. 4,877,896) groups polyester polyurethanes obtained by reaction of a polyester with a number-average molecular mass of 300–4000, obtained from adipic acid and/or from terephthalic acid and/or from sulphoisophthalic acid and from a diol with a mass of less than 300, with a prepolymer containing terminal isocyanate groups obtained from a poly(ethylene glycol) with a molecular mass of 600–4000 and from a diisocyanate (FR-A-2,334,698)

ethoxylated monoamines or polyamines or polymers of ethoxylated amines (U.S. Pat. No. 4,597,898 and EP-A-11,984)

sulphonated polyester oligomers obtained by condensation of isophthalic acid, of dimethyl sulphosuccinate and of diethylene glycol (FR-A-2,236,926).

The performances of the cosmetic compositions forming the subject-matter of the invention can also be improved by the use of plasticizers. The plasticizer can constitute between 0.1 and 20% of the formulation, preferably from 1 to 15%. Mention may be made, among particularly useful plasticizers, of adipates, phthalates, isophthalates, azelates, stearates, silicone copolyols, glycols, castor oil or their mixtures.

It is also advantageously possible to add, to these compositions, metal-sequestering agents, more particularly those sequestering calcium, such as citrate ions, or emollients, such as silicones or oils or fatty substances used in this connection in the cosmetics industry (mineral oils, fatty acid esters, triglycerides, silicones, and the like).

It is also possible to add water-soluble or water-dispersible polymers, such as collagen or certain non-allergizing derivatives of animal or plant proteins (wheat protein hydrolysates, for example), natural hydrocolloids (guar gum, locust bean gum, tara gum, and the like) or hydrocolloids resulting from fermentation processes, such as xanthan gum, and derivatives of these polycarbohydrates, such as modified celluloses (for example, hydroxyethylcellulose or carboxymethylcellulose), or guar or locust bean derivatives, such as their cationic derivatives or non-ionic derivatives (for example, hydroxypropylguar) or anionic derivatives (carboxymethylguar and carboxymethylhydroxypropylguar).

Inorganic powders or particles, such as calcium carbonate, inorganic oxides in the powder form or in the colloidal form (particles with a size of less than or of the order of a micrometre, sometimes of a few tens of nanometres), such as silica, aluminium salts generally used as antiperspirants, kaolin, talc, clays and their derivatives, and the like, can be added in combination to these compounds.

One or more fragrances, colouring agents, among which may be mentioned the products described in Appendix IV ("List of colouring agents allowed for use in cosmetic products") of European Directive No. 76/768/EEC of Jul. 27, 1976, known as the cosmetic directive, and/or opacifying agents, such as pigments, can generally be added to these ingredients to increase the attractiveness during use of the composition by the consumer.

Finally, the composition can also contain viscosifying or gelling polymers, such as crosslinked polyacrylates (Carbopol, sold by Goodrich), cellulose derivatives, such as hydroxypropylcellulose or carboxymethylcellulose, guars and their derivatives, locust bean, tara or cassia gum, xanthan gum, alginates, carrageenans, or chitin derivatives, such as chitosan, used alone or in combination, or the same compounds, generally in the form of water-soluble polymers modified by hydrophobic groups bonded covalently to the polymer skeleton, as described in Patent WO 92/16187, and/or water, in order to bring the total of the constituents of the formulation to 100%.

The cosmetic compositions forming the subject-matter of the invention can also comprise polymeric dispersing agents in an amount of the order of 0.1 to 7% by weight, in order to control the calcium and magnesium hardness, agents such as:

water-soluble salts of polycarboxylic acids with a molecular mass of the order of 2000 to 100,000, obtained by polymerization or copolymerization of ethylenically unsaturated carboxylic acids, such as acrylic acid, maleic acid or anhydride, fumaric acid, itaconic acid, aconitic acid, mesaconic acid, citraconic acid or methylenemalonic acid, and very particularly polyacrylates with a molecular mass of the order of 2000 to 10,000 (U.S. Pat. No. 3,308,067) or copolymers of acrylic acid and of maleic anhydride with a molecular mass of the order of 5000 to 75,000 (EP-A-66,915)

poly(ethylene glycol)s with a molecular mass of the order of 1000 to 50,000.

The following examples illustrate the invention without, however, limiting the scope thereof.

EXAMPLES

Example 1

Preparation of a Dispersion of Particles According to the Invention with a Silica-based Treatment Preparation of the Starting Particles The following are successively added to 1300 g of a 1.73 mol/kg titanium oxychloride solution:

121 g of 36% hydrochloric acid, 15.14 g of citric acid, 1562 g of purified water, 10.30 g (3.6%/$TiO_2$) of anatase seeds exhibiting a size of between 5 and 6 nm.

The mixture is brought to boiling point and is maintained there for 3 h.

The solution is subsequently filtered and the particles obtained are washed with water until the chlorides have been completely removed. They are subsequently redispersed at pH 9 (controlled by the addition of sodium hydroxide) with a solids content of 20% by weight.

The size of the particles, measured by TEM, is 60 nm. X-ray diffraction analysis shows that the particles are based on titanium dioxide solely in the anatase form.

The relative density is 2.52 (Vi=0.14 cc/g).

The specific surface, measured by the BET method on the particles of the dispersion dried at a degassing temperature of 150° C., is 300 $m^2/g$.

Treatment of the Particles with Silica 750 g of the above dispersion are introduced with stirring into 750 g of deionized water.

The mixture obtained is transferred into a reactor and the temperature is raised to 90° C. The pH is adjusted to 9 by the addition of sodium hydroxide.

A sodium silicate solution (solution containing 335 g/l of $SiO_2$), containing the equivalent of 30 g of $SiO_2$, and an 80 g/l sulphuric acid solution are introduced therein continuously and simultaneously. The flow rate of the alkali metal silicate solution is set at 2 ml/min and the pH is regulated at 9 by the addition of sulphuric acid.

After introducing the reactants, the temperature is maintained at 90° C. for 2 h.

After cooling, the dispersion is centrifuged. The cake obtained is washed three times with water and then redispersed at pH 8.5 with a solids content of 40% by weight.

Properties of the Particles Obtained

The size of the particles, measured by TEM, is 60 nm.

The specific surface, measured by the BET method on the particles of the dispersion which have been dried under vacuum at a temperature of 150° C. for 4 hours, is 140 $m^2/g$.

The level of $SiO_2$, measured by X-ray fluorescence, is 19% by weight with respect to the titanium dioxide.

The relative density is 2.2.

The viscosity is 750 mPa·s.

The dispersion index is 0.45. This dispersion is particularly stable: after one month, the measurement of the dispersion index remains at 0.45.

Example 2

Preparation of a Dispersion of Particles According to the Invention with a Treatment Based on Silica and on Aluminium Hydroxide The starting particles are the same as in Example 1.

Treatment of the Particles with Silica and with Aluminium Oxide, Hydroxide or Hydroxide Oxide 750 g of the starting dispersion are introduced into a reactor with a stirrer. 750 g of purified water are then added and the temperature is raised to 90° C. The pH of the dispersion is adjusted to 9 by the addition of sodium hydroxide.

First of all, a sodium silicate solution (solution containing 335 g/l of $SiO_2$), containing the equivalent of 22.5 g of $SiO_2$, and an 80 g/l sulphuric acid solution, in an amount such that the pH is maintained at 9, are introduced continuously and simultaneously. The flow rate of the sodium silicate solution is set at 2 ml/min. A maturing time of 1 h at 90° C. is subsequently observed.

Subsequently, an aqueous sodium aluminate solution (solution containing 240 g/l as $Al_2O_3$), containing the equivalent of 7.5 g of $Al_2O_3$, is introduced continuously at pH 9 and at 90° C. The flow rate of the aluminate solution is 2 ml/min and the pH is regulated at 9 by simultaneous introduction of a 6N aqueous sulphuric acid solution.

When the reactants have been introduced, a maturing time of 2 h at 90° C. is observed and then the dispersion is cooled.

The dispersion obtained is centrifuged. The cake obtained is washed three times with water and is then redispersed.

The pH of the dispersion is adjusted to 7.5 by addition of $H_2SO_4$ and it exhibits a solids content of 30% by weight.

Properties of the Particles Obtained

The size of the particles, measured by TEM, is 60 nm.

The specific surface, measured by the BET method on the particles of the dispersion which have been dried under vacuum at a temperature of 150° C., is 135 $m^2/g$.

The level of $SiO_2$, measured by X-ray fluorescence, is 14.9% by weight and that of $Al_2O_3$ is 5%.

The viscosity is 750 mPa·s.

The relative density is 2.15.

The dispersion index is 0.45. This dispersion is particularly stable: after one month, the measurement of the dispersion index remains at 0.45.

Example 3

Stability of the Dispersion of Example 2 as a Function of the pH

The pH of the dispersion of Example 2 is varied by addition of sulphuric acid or sodium hydroxide. The dispersion indices associated with each pH are combined in the following table.

| pH | dispersion index |
|---|---|
| 5.5 | 0.43 |
| 6.5 | 0.35 |
| 7.5 (Ex. 2) | 0.45 |
| 8 | 0.31 |
| 10 | 0.31 |

It is observed that, for a pH varying from 5.5 to 10, the dispersion index remains below 0.45.

Example 4

Anti-UV Cosmetic Preparation

An anti-UV cosmetic composition according to the invention is prepared from the titanium dioxide dispersion of Example 3, the following formulation being followed:

| CTFA | Ingredients | % by weight |
|---|---|---|
| cyclomethicone and diphenyl dimethicone | Mirasil C-DPDM | 4 |
| caprylic/capric triglyceride | Miglyol 812 N | 4 |
| octyl palmitate | Crodamol OP | 4 |
| mineral oil | Marcol 82 | 5 |
| PVP/eicosene copolymer | Antaron V220 | 3 |
| vitamin E acetate | | 0.3 |
| glyceryl stearate | | |
| propylene glycol stearate | | |
| glyceryl isostearate | Hydrolactol 70 | 10 |
| propylene glycol isostearate | | |
| oleth-25 | | |
| ceteth-25 | | |
| potassium cecyl phosphate | Amphisol K | 2 |
| polysorbate 20 | Tween 20 | 1 |
| preservative | Germaben II | 0.2 |
| allantoin | | 0.2 |
| xanthan gum | Rhodicare D | 0.2 |
| dispersion, Example 2 | | 15.6 (5% as TiO$_2$) |
| lactic acid | | q.s. pH = 6.5 |
| deionized water | | q.s. 100 |

Measurement of Photostability of the Composition

The cosmetic composition to be tested is introduced via a quartz cell into a Heraeus Sun-Test device and subjected to energy E of 500 W/m$^2$ at a temperature T of 30° C. for 1 h.

The photostability is monitored by visual observation of the colouring of the formulation. Visually, no blueing is observed.

Measurement of the in vitro SPF (Sun Protection Factor) Number

This number was measured using an SPF290 optometry device according to the method described in "Cosmetics & Toiletries", Vol. 107, No. 10, p.119.

The SPF number is 20±2 for an application of 2 mg/cm$^2$.

Measurement of the Dispersion Index of the Titanium Dioxide Particles in the Formulation The dispersion index is 0.45, that is to say identical to that of the dispersion of titanium dioxide particles before formulation.

What is claimed is:

1. A process for preparing a stable aqueous dispersion, with a solids content at least 35% by weight, of titanium dioxide particles having a largely anatase crystalline structure, wherein at least one metal oxide, hydroxide or hydroxide oxide is precipitated at the surface of the titanium dioxide particles while in a dispersion, the particles having a mean diameter of at most 100 nm, said titanium dioxide particles being at least partially covered with a layer of at least one of said metal oxide, hydroxide or hydroxide oxide, the covered particles exhibiting a BET specific surface of at least 70 m$^2$/g.

2. The process according to claim 1, wherein at least one metal oxide, hydroxide or hydroxide oxide is precipitated at the surface of titanium dioxide particles obtained by hydrolysis of at least one titanium compound A in the presence of at least one compound B selected from the group consisting of:
   (i) acids which exhibit:
      either a carboxyl group and at least two hydroxyl and/or amine groups,
      or at least two carboxyl groups and at least one hydroxyl and/or amine group,
   (ii) organic phosphoric acids of following formulae:

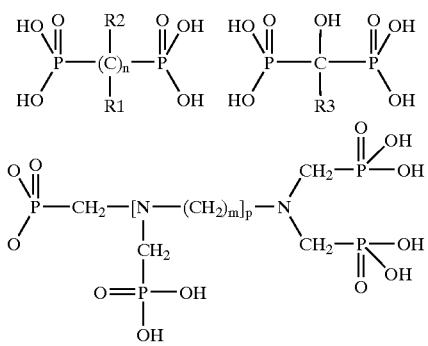

in which n and m are integers of between 1 and 6 and p is an integer of between 0 and 5, R1, R2 and R3, which are identical or different, representing a hydroxyl, amino, aralkyl, aryl or alkyl group or hydrogen,
   (iii) compounds capable of releasing sulphate ions in acidic medium, and
   (iv) salts of the acids described above,
      and in the presence of anatase titanium dioxide seeds exhibiting a size of at most 5 nm and in a titanium, expressed as TiO$_2$, present in the seeds/titanium present before introduction of the seeds in the hydrolysis medium, expressed as TiO$_2$, ratio by weight of between 0.01% and 3%.

3. Process according to claim 2, wherein the titanium compound A is titanium oxychloride.

4. Process according to claim 2, wherein the compound B is citric acid.

5. A method for minimizing the effects of ultraviolet radiation, said method comprising preparing a dispersion comprising anatase titanium dioxide particles by the process according to claim 1, adding the dispersion to a composition, and applying the composition to a patient in need of such minimization.

6. A process for minimizing the effects of ultraviolet radiation on the surfaces of an object, said process comprising forming a dispersion comprising anatase titanium dioxide according to the process of claim 1, adding the dispersion to a paint or varnish composition, and applying the paint or varnish composition to the surface of an object.

7. The process according to claim 1, wherein the ratio by weight of the metal oxide, hydroxide or hydroxide oxide to the titanium dioxide is at most 60% by weight.

8. The process according to claim 1, wherein silica or aluminum oxide, hydroxide or hydroxide oxide is precipitated in a simple or mixed form.

9. The process according to claim 8, wherein silica and aluminum oxide, hydroxide or hydroxide oxide are precipitated in amounts by weight of 15% of $SiO_2$ and 5% of $Al_2O_3$ with respect to titanium dioxide.

10. The process according to claim 1, wherein the dispersion index of the particles in the liquid phase is at most 0.5.

11. The process according to claim 1, wherein the dispersion exhibits a conductivity of at most 3 msiemens.

12. The process according to claim 1, wherein the particles exhibit a BET specific surface of at least 200 $m^2/g$ prior to being at least partially covered.

13. A process for preparing an anti-UV cosmetic composition, comprising the step of introducing into a cosmetic formulation a dispersion of anatase titanium dioxide particles, prepared by the process according to claim 1.

14. A process for preparing an anti-UV cosmetic composition, comprising the step of introducing into a cosmetic formulation a dispersion of anatase titanium dioxide particles, prepared by the process according to claim 1, said dispersion having a solids contents of at least 35% by weight, and the viscosity of said dispersion being at most 1000 mPa·s.

15. A method of making a stable aqueous dispersion having a solids content of at least 35% by weight, without use of a dispersing agent, the method comprising the steps of:
(i) forming starting titanium dioxide particles with a largely anatase crystalline structure having a mean diameter no greater than 100 nm by hydrolyzing a solution comprising a titanium compound, a second compound, and titanium dioxide seeds, the titanium dioxide seeds having a size less than 8 nm, and the amount of titanium dioxide provided by the titanium dioxide seeds in the starting solution is 0.01–3.0% by weight;
(ii) adding at least one precursor of a metal oxide, hydroxide, or hydroxide oxide to the solution thereby forming a mixture; and
(iii) modifying the pH of the mixture formed in step (ii) thereby precipitating at least one metal oxide, hydroxide or hydroxide oxide coating at least partially covering the starting titanium dioxide particles thereby forming a stable aqueous dispersion of coated titanium dioxide particles;
wherein the coated titanium dioxide particles are present in an amount sufficient to provide the dispersion with at least 35% by weight suspended solids, and wherein the dispersion is formed without the addition of a dispersing agent.

16. The method of claim 15, wherein the starting titanium dioxide particles are provided with a BET surface area of at least 200 $m^2/g$.

17. The method of claim 15, wherein the coated titanium dioxide particles are provided with a BET surface area of at least 70 $m^2/g$.

18. The method of claim 15, wherein the dispersion is provided with a viscosity of less than 1,000 mPa·s.

19. The method of claim 15, wherein the anatase crystalline structure is greater than 80% anatase.

20. The method of claim 15, wherein the starting titanium dioxide particles are provided with a mean diameter of 50–70 nm.

21. The method of claim 15, wherein the at least one metal oxide, hydroxide, or hydroxide oxide is precipitated in simple or mixed form.

22. The method of claim 15, wherein the coated titanium dioxide particles are formed such that they comprise at most 60% by weight of the metal oxide, hydroxide or hydroxide oxide.

23. The method of claim 15, wherein the dispersion is provided with a conductivity of at most 3 msiemens.

24. The method of claim 15, wherein the dispersion is formed with at least 40% suspended solids.

25. The method of claim 15, wherein the dispersion is provided with a dispersion index of no greater than 0.5.

26. The method of claim 15, wherein the dispersion is provided with a dispersion index of no greater than 0.5 over a pH range of 5.5 to 10.

27. The method of claim 15, wherein the titanium compound of step (i) is chosen from at least one of titanium halides, oxyhalides, alkoxides and sulphates.

28. The method of claim 15, wherein the second compound is chosen from the group of:
(i) acids which exhibit:
either a carboxyl group and at least two hydroxyl and/or amine groups,
or at least two carboxyl groups and at least one hydroxyl and/or amine group,
(ii) organic phosphoric acids of following formulae:

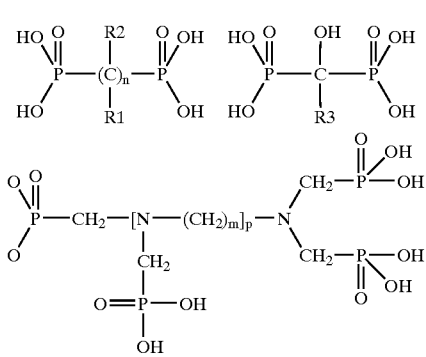

in which n and m are integers of between 1 and 6 and p is an integer of between 0 and 5, R1, R2 and R3, which are identical or different, representing a hydroxyl, amino, aralkyl, aryl or alkyl group or hydrogen,
(iii) compounds capable of releasing sulphate ions in acidic medium, and
(iv) salts of the acids described above.

29. The method of claim 15, wherein the titanium dioxide seeds of step (i) have a size of 3 to 5 nm.

30. The method of claim 15, wherein the starting solution is formulated such that the amount of titanium dioxide provided by the titanium dioxide seeds in the starting solution is 0.05–1.5% by weight.

31. The method of claim 15, wherein the method comprises the additional steps of neutralizing and washing the starting titanium dioxide particles between steps (ii) and (iii).

32. The method of claim 15, wherein the starting solution is completely aqueous.

33. The method of claim 15, wherein steps (iv) and (v) comprise least partially coating the starting titanium dioxide particles with silica and an aluminum oxide, hydroxide or hydroxide oxide, in simple or mixed form.

34. A method of forming a cosmetic composition, the method comprising forming a stable aqueous dispersion according to claim 15, and combining the dispersion with at least one vehicle.

35. The method of claim 34, wherein the amount of the dispersion added is such that the cosmetic composition comprises 1–25% by weight titanium dioxide.

36. The method of claim 34, wherein the amount of vehicle added is such that the cosmetic composition comprises 10–99% by weight of the vehicle.

37. The method of claim 34, further comprising adding one or more of the following components to the cosmetic composition: an oil, an emulsifier, a surface active agent, an organic sunscreen, an inorganic sunscreen, a preservative, an antioxidant, a humectant, a buffer solution, a wax, a plant extract, a fixative resin, a polymeric derivative exercising a protective function, a plasticizer, a metal-sequestering agent, an animal or plant derived protein, inorganic particles, a fragrance, a coloring agent, a viscifying or gelling polymer, and a polymeric dispersing agent.

38. The process of claim 1, wherein the dispersion is produced with a viscosity of less than 1,000 mPa·S.

* * * * *